(12) United States Patent
Du et al.

(10) Patent No.: US 11,364,078 B2
(45) Date of Patent: Jun. 21, 2022

(54) ELECTRO-OPTIC Q-SWITCHING DOUBLE-FREQUENCY DOUBLE-PULSE LASER LITHOTRIPSY SYSTEM

(71) Applicant: Jilin Province King Laser Co., Ltd., Jilin (CN)

(72) Inventors: Jinbo Du, Jilin (CN); Jianhua Shao, Jilin (CN); Jiazuo Dong, Jilin (CN); Lingtian Diao, Jilin (CN)

(73) Assignee: Jilin Province King Laser Co., Ltd., Jilin (CN)

( * ) Notice: Subject to any disclaimer, the term of this patent is extended or adjusted under 35 U.S.C. 154(b) by 0 days.

(21) Appl. No.: 16/762,919

(22) PCT Filed: Apr. 26, 2019

(86) PCT No.: PCT/CN2019/084444
§ 371 (c)(1),
(2) Date: May 9, 2020

(87) PCT Pub. No.: WO2020/103399
PCT Pub. Date: May 28, 2020

(65) Prior Publication Data
US 2021/0267684 A1   Sep. 2, 2021

(30) Foreign Application Priority Data
Nov. 20, 2018  (CN) .......................... 201811381556.4

(51) Int. Cl.
*A61B 18/26* (2006.01)
*H01S 3/115* (2006.01)
(Continued)

(52) U.S. Cl.
CPC .............. *A61B 18/26* (2013.01); *H01S 3/115* (2013.01); *H01S 3/1643* (2013.01); *A61B 2018/00511* (2013.01)

(58) Field of Classification Search
CPC .......... A61B 18/26; A61B 2018/00511; A61B 2018/00517; A61B 18/20–18/28;
(Continued)

(56) References Cited

U.S. PATENT DOCUMENTS 5,408,480 A * 4/1995 Hemmati ................ H01S 3/113
372/10
7,792,162 B2 * 9/2010 Piper ...................... H01S 3/1086
372/20
(Continued)

FOREIGN PATENT DOCUMENTS

CN        2571411 Y     9/2003
CN      201075571 Y     6/2008
(Continued)

OTHER PUBLICATIONS

Dong, Jian, et al. "High power diode-side-pumped Q-switched Nd:YAG solid-state laser with a thermoelectric cooler." Applied Sciences 5.4 (2015): 1837-1845. https://doi.org/10.3390/app5041837 ; Published Dec. 16, 2015 (Year: 2015).*
(Continued)

*Primary Examiner* — Jonathan T Kuo
(74) *Attorney, Agent, or Firm* — Yu Gang

(57) ABSTRACT

The present disclosure discloses an electro-optic Q-switching double-frequency double-pulse laser lithotripsy system. The system includes a total reflection mirror, an electro-optic Q-switching assembly, a drive circuit, a controller, a pump source, a gain medium, an output mirror, a first focusing mirror, a frequency doubling crystal, a second focusing mirror, a coupling lens and an output optical fiber; the electro-optic Q-switching assembly and the gain medium are located between the total reflection mirror and the output mirror; and the controller controls the pump source to work, and controls a voltage of the electro-optic Q-switching assembly by controlling the drive circuit, so that the system (Continued)

outputs a double-frequency laser beam with a pulse width of 1-1.5 μs or 200-300 μs.

10 Claims, 4 Drawing Sheets

(51) Int. Cl.
*H01S 3/16* (2006.01)
*A61B 18/00* (2006.01)

(58) Field of Classification Search
CPC ............... H01S 3/115; H01S 3/1643; A61N 5/06–2005/073
See application file for complete search history.

(56) References Cited

U.S. PATENT DOCUMENTS

2008/0259969 A1* 10/2008 Piper .................. H01S 3/1086 372/20

2015/0342678 A1   12/2015   Deladurantaye et al.

FOREIGN PATENT DOCUMENTS

| | | |
|---|---|---|
| CN | 201853942 U | 6/2011 |
| CN | 102525650 A | 7/2012 |
| CN | 103427325 A | 12/2013 |
| CN | 104253375 A | 12/2014 |
| CN | 106913961 A | 4/2017 |
| CN | 107994457 A | 5/2018 |
| CN | 109512576 A | 3/2019 |
| DE | 4310023 A1 | 9/1994 |
| WO | 9423478 A2 | 10/1994 |
| WO | 9423478 A3 | 1/1995 |

OTHER PUBLICATIONS

W.O.M World Of Medicine Gmbh: "U100plus: The Lithotripsy Laser", Sep. 1, 2013, pp. 1-4, XP055771434.

* cited by examiner

ELECTRO-OPTIC Q-SWITCHING DOUBLE-FREQUENCY DOUBLE-PULSE LASER LITHOTRIPSY SYSTEM

CROSS-REFERENCE TO RELATED APPLICATIONS

The present application claims priority to the Chinese Patent Application No. 201811381556.4, filed to the Chinese Patent Office on Nov. 20, 2018, and entitled "ELECTRO-OPTIC Q-SWITCHING DOUBLE-FREQUENCY DOUBLE-PULSE LASER LITHOTRIPSY SYSTEM", tie contents of which are incorporated herein by reference in its entirety.

TECHNICAL FIELD

The present disclosure relates to the technical field of optic-based medical apparatus and instruments, and in particular to an electro-optic Q-switching double-frequency double-pulse laser lithotripsy system.

BACKGROUND

In order to crush a stone in a digestive system and a urinary system, a variety of methods have been invented by human beings, such as an extracorporeal shock wave lithotripsy, an electrohydraulic lithotripsy, an ultrasonic lithotripsy and a laser lithotripsy. Because of many inherent advantages of the laser lithotripsy, in addition to the first choice of the extracorporeal shock wave lithotripsy for a kidney stone, other methods have been basically replaced by the laser lithotripsy in clinical practice. Moreover, in the laser lithotripsy, a Ho:Cr:Tm:YAG 2.1-µm static laser and a Nd:YAG 1.064+0.532-µm double-frequency double-pulse Q-switching laser are used clinically at present.

The above two lithotripters have completely different action mechanisms. A stone crushing action of the Q-switching double-frequency double-pulse Nd:YAG laser lies in that after a stone is irradiated by a laser at a high power density, an atom volatilized on a surface is ionized by a high-energy laser photon and forms a plasma quickly, then the plasma absorbs subsequent laser energy, expands and collides quickly, and the stone may be crushed by generated shock wave and microjet. A holmium laser absorbs extremely large laser energy mainly by virtue of water and a stone, to generate thermal drilling and thermal blasting. Compared with a holmium laser lithotripsy system that is used extensively, the Q-switching Nd:YAG laser may implement a high peak power (about $1*10^5$ W) just by the use of small energy (about 100 mJ), and even 1000 pulses are impacted on a ureteral wall, no damage will be caused to this soft tissues. Usually, the energy of the holmium laser lithotripsy is up to about 1000-3000 mJ but the peak power is merely $1*10^4$ W. In a general case, once an optical fiber is not aligned to the stone but impacted on the ureteral wall, the ureteral wall will be perforated just by one pulse. As a result, the holmium laser lithotripter produced in China presently can only be used for crushing a stone with a large size, and has a poor effect and a large risk to a small stone.

A Q-switching Nd:YAG laser lithotripsy system (U-100 and U-100Plus, the later is an updated version of the former) is disclosed in the conventional art. As shown in FIG. 1, an optical fiber that is 20-30 m long is used in an optical path, and configured to prolong a length of a laser resonant cavity; and meanwhile, a passive Q-switching crystal is used to compress a laser pulse width, to output a 1 µs laser pulse finally. Nevertheless, such a structure has the following defects: firstly, to change an output pulse width, the length of the optical fiber in the optical path needs to be changed necessarily, which requires a complex adjustment of the system, and this is impossible in clinical practice; secondly, the passive Q-switching crystal is used in the structure to realize an output a 1 µs laser the resonant cavity of the passive Q-switching has a very high loss, so the electro-optic efficiency of the whole machine is low; and thirdly, with the use of the long optical fiber and the Cr4+:YAG passive Q-switching, such a structure only can output a 1 µs dynamic stone crushing pulse. However, in actual clinical practice, a case where a layer of soft tissue structure covers a periphery of the stone occurs sometimes. Before the lithotripsy, the soft tissue must be vaporized and stripped, which cannot be made possible by the lithotripter.

Therefore, there is a lack of a laser lithotripsy system that can crush a stone, can also implement cutting of a soft tissue around the stone, and has high electro-optic efficiency and easy to change a pulse width.

SUMMARY

In order to solve the above-mentioned problems, the present disclosure provides an electro-optic Q-switching double-frequency double-pulse laser lithotripsy system.

The technical solution used by the present disclosure to solve the technical problem is as follows.

An electro-optic Q-switching double-frequency double-pulse laser lithotripsy system includes a total reflection mirror, an electro-optic Q-switching assembly, a drive circuit, a controller, a pump source, a gain medium, an output mirror, a first focusing mirror, a frequency doubling crystal, a second focusing mirror, a coupling lens and an output optical fiber; the electro-optic Q-switching assembly and the gain medium are located between the total reflection mirror and the output mirror; the drive circuit is connected to the electro-optic Q-switching assembly; and the controller is connected to the electro-optic Q-switching assembly and the pump source, the controller controls the pump source to work, and the controller controls a voltage of the electro-optic Q-switching assembly by controlling the drive circuit.

The controller controls the pump source to generate pump light to irradiate the gain medium; the controller controls the drive circuit; when a voltage difference exists on the electro-optic Q-switching assembly, an optical resonant cavity is formed between the total reflection mirror and the output mirror; when the pump light passes through the optical resonant cavity and a gain of the pump light reaches a threshold, a laser beam is output by the output mirror; the laser beam is sequentially converged by the first focusing mirror, partially doubled in frequency by the frequency doubling crystal, and then emitted in parallel via the second focusing mirror, converged and coupled by the coupling lens, and output through the output optical fiber; and the laser beam is a dynamic laser beam with a pulse width of 1 µs-1.5 µs or a static laser beam with a pulse width of 200 µs-300 µs.

Further, when the voltage of the electro-optic Q-switching assembly gradually increases or decreases, a loss of the electro-optic Q-switching assembly gradually decreases, and the loss of the electro-optic Q-switching assembly keeps a dynamic balance with a gain of the gain medium all the time, the output mirror outputs the laser beam with the pulse width of 1 µs-1.5 µs; and when the voltage of the electro-optic Q-switching assembly is λ/4, the output mirror outputs the laser beam with the pulse width of 200 µs-300 µs, wherein the λ denotes a wavelength of the laser beam output by the output mirror.

Further, the electro-optic Q-switching assembly includes a Pockel cell and a polarizer, and the drive circuit is connected to two ends of the Pockel cell.

Further, the electro-optic Q-switching assembly further includes a quarter wave plate, the quarter wave plate is located between the total reflection mirror and the Pockel cell, and when a voltage of the two ends of the Pockel cell gradually decreases, a loss of the Pockel cell gradually decreases and the loss of the Pockel cell keeps a dynamic balance with the gain of the gain medium all the time, the laser beam with the pulse width of 1 µs-1.5 µs is output.

Further, the drive circuit includes a shaping circuit connected to the controller, a delay drive circuit connected to the shaping circuit, a voltage dropping circuit connected to the delay drive circuit and one end of the Pockel cell, and a constant voltage circuit connected to other end of the Pockel cell, the voltage dropping circuit includes a second direct-current high-voltage power supply, N voltage-dropping sub-circuits and a second ground terminal that are serially connected in sequence, the second direct-current high-voltage power supply is serially connected to the N voltage-dropping sub-circuits, the delay drive circuit includes N delay drive sub-circuits, and the delay drive sub-circuits are connected to the voltage-dropping sub-circuits in one-to-one correspondence, N≥3.

Further, the constant voltage circuit includes a first ground terminal.

Further, the constant voltage circuit further includes a first direct-current high-voltage power supply, a high-voltage switch connected to an output end of the first direct-current high-voltage power supply, and a filter circuit connected to the high-voltage switch, and the first ground terminal is connected to the filter circuit.

Further, the filter circuit is formed by a capacitor and a resistor in parallel connection.

Further, the voltage-dropping sub-circuit includes a voltage-division Metal Oxide Semiconductor (MOS) switch, a voltage-division capacitor and a discharge current limiting resistor that are connected sequentially, and the voltage-division MOS switch is connected to a corresponding delay drive sub-circuit.

Further, the pump source is a xenon lamp, and the gain medium is a Nd:YAG crystal.

The present disclosure has the following beneficial effects.

1. By controlling a drive circuit and a pump source via a controller, an optical resonant cavity can output a laser beam with an a pulse width of 1 µs-1.5 µs, and can also output a laser beam with a pulse width of 200 µs-300 µs. A stone can be crushed through the output dynamic laser beam of 1 µs-1.5 µs, and a soft tissue around the stone can be cut through the output static laser beam with the pulse width of 200 µs-300 µs.

2. Switching of lasers with different pulse widths does not need a complex replacement of an optical fiber in an optical path, may be implemented only by controlling a drive circuit switch via a controller and controlling a voltage of an electro-optic Q-switching assembly via the drive circuit switch, and does not need a complex adjustment of the optical path, the pulse width is easy to change, the structure is simple, the use is convenient, and is suitable for clinical practice.

3. The electro-optic Q-switching assembly is used in the optical resonant cavity to output the laser with the pulse width of 1-1.5 µs, so a loss of the resonant cavity is decreased, that is, a threshold is decreased, and an electro-optic efficiency is improved.

4. The present disclosure realizes the output of lasers with two wavelengths via one optical path system, the short-wave laser has higher photon energy, which is conductive to the ignition of a plasma, long-wave energy is absorbed by the plasma, and the strength of a stone crushing is enhanced, and the lasers with two different wavelengths are adapted to different stages of the lithotripsy, and can achieve a good stone crushing effect.

5. According to the electro-optic Q-switching double-frequency double-pulse laser lithotripsy system provided by the present disclosure, through a manner in which a sub-pulse laser beam is output by closely following a main pulse laser beam, as sub-pulse laser energy is absorbed by the generated plasma, a stone crushing strength of a shock wave is greatly enhanced; and therefore, the present disclosure may crush a cystine stone that is white and hard and cannot be crushed by a previous lithotripter.

In the figures: 1. total reflection mirror, 2. a quarter wave plate, 3. Pockel cell, 4. drive circuit, 4011. first direct-current high-voltage power supply, 4012. high-voltage switch. 4013. filter circuit, 402. voltage dropping circuit, 4021. second direct-current high-voltage power supply, 4022. voltage dropping sub-circuit, 403. delay drive circuit, 4031. delay drive sub-circuit, 404. shaping circuit, 5. polarizer, 6. solid laser bar, 7. output mirror, 8. first focusing mirror, 9. second focusing mirror, 10. coupling lens, 11. output optical fiber, 12. frequency doubling crystal, 13. pump source, and 14. controller.

DETAILED DESCRIPTION OF THE EMBODIMENTS

In order to understand the above objectives, features and advantages of the present disclosure more clearly, the present disclosure is further described below in detail in combination with accompanying drawings and specific embodiments.

Many particular details are elaborated in the following description for the easy of a full understanding of the present disclosure. However, the present disclosure may further be implemented in other manners different from those described herein. Therefore, a protection scope of the present disclosure is not limited by the following disclosed specific embodiments.

Figure 1:
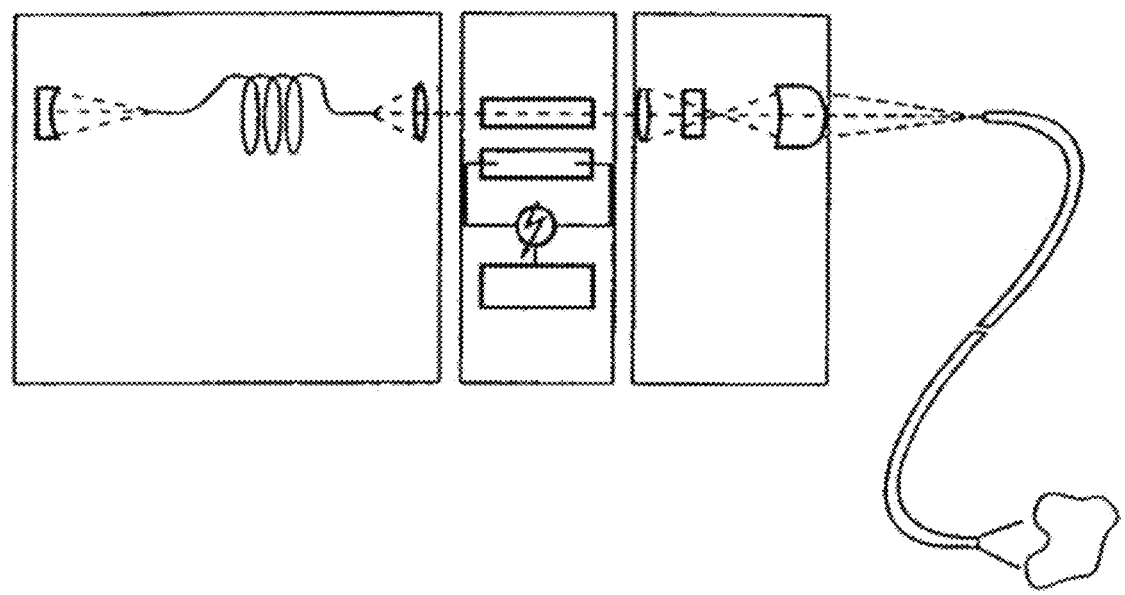
FIG. 1 is a structural diagram of a U-100 laser lithotripsy system of German WOM company.
Figure 2:
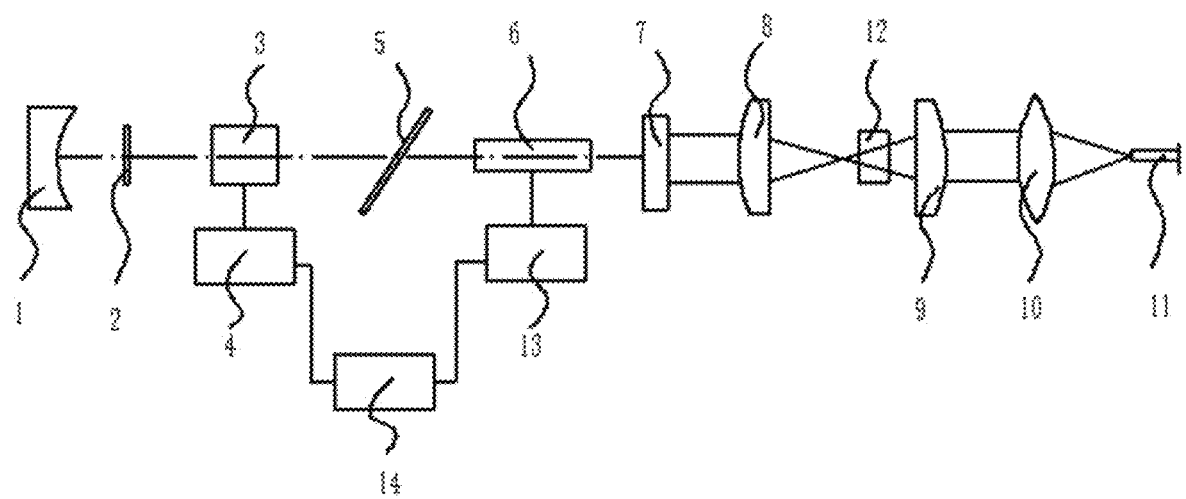
FIG. 2 is a schematic diagram of a voltage increasing type Q-switching optical path of the present disclosure.

An electro-optic Q-switching double-frequency double-pulse laser lithotripsy system includes a total reflection mirror 1, an electro-optic Q-switching assembly, a drive circuit 4, a controller 14, a pump source 13, a gain medium 6, an output mirror 7, a first focusing mirror 8, a frequency doubling crystal 12, a second focusing mirror 9, a coupling lens 10 and an output optical fiber 11. As shown in FIG. 2, the electro-optic Q-switching assembly and the gain medium 6 are located between the total reflection mirror 1 and the output mirror 7. The drive circuit 4 is connected to the electro-optic Q-switching assembly, to control the electro-optic Q-switching assembly to open and close. The controller 14 is connected to the electro-optic Q-switching assembly and the pump source 13, the controller 14 controls the pump source 13 to work, and the controller 14 controls the drive circuit 4, and controls, via the drive circuit 4, a voltage acted on the electro-optic Q-switching assembly.

The controller 14 controls the pump source 13 to pump; the pump source 13 generates pump light to irradiate the gain medium 6; the controller 14 controls the drive circuit 4; when a voltage difference exists on the electro-optic Q-switching assembly, an optical resonant cavity is formed between the total reflection mirror 1 and the output mirror 7; when the pump light passes through the optical resonant cavity and a gain of the pump light reaches a threshold, a laser beam is output by the output mirror 7; and at this time, the laser beam output by the output mirror 7 is a laser beam with a pulse width of 1 μs-1.5 μs or a laser beam with a pulse width of 200 μs-300 μs. The laser beam output from the output mirror 7 is converged by the first focusing mirror 8 and then projected to the frequency doubling crystal 12, partially doubled in frequency by the frequency doubling crystal 12 (since the frequency doubling crystal 12 has a frequency doubling efficiency, one part of laser beam is doubled in frequency, and the other part of laser beam keeps unchanged in frequency) and projected to the second focusing mirror 9, emitted to the coupling lens 10 in parallel after passing through the second focusing mirror 9, converged and coupled by the coupling lens 10 and then transmitted to the output optical fiber 11, and output from the system via the output optical fiber 11, for medical treatment. The laser beam output from the output mirror 7 passes through the frequency doubling crystal 12, so that the laser beam with the pulse width of 1 μs-1.5 μs or the laser beam with the pulse width of 200 μs-300 μs becomes a double-frequency laser beam to output.

The electro-optic Q-switching double-frequency double-pulse laser lithotripsy system provided by the present disclosure controls a drive circuit 4 and a pump source 13 via a controller 14, so that an optical resonant cavity can output a dynamic laser beam with a pulse width of 1 μs-1.5 μs, and the dynamic laser beam with such a pulse width can crush a stone; with the control of the controller 14, the optical resonant cavity can output a static laser beam with a pulse width of 200 μs-300 μs, and the static laser beam with such a pulse width can cut a soft tissue around the stone. Therefore, the laser lithotripsy system of the present disclosure not only may crush the stone, but also can remove the soft tissue around the stone. Meanwhile, once an output optical fiber 11 is not aligned to the stone, no damage will be caused to a human body, for example, once the output optical fiber 11 is impacted on a ureteral wall, the wall is not perforated to achieve a high safety. In addition, as the output optical fiber 11 is not used in the optical resonant cavity, switching of lasers with different pulse widths does not need a complex replacement of the output optical fiber 11 in an optical path, may be implemented only by controlling the drive circuit 4 via the controller 14 and controlling an electro-optic Q-switching assembly via the drive circuit switch 4, and does not need a complex adjustment of the optical path, the pulse width is easy to change, and the present disclosure is suitable for clinical practice. The electro-optic Q-switching assembly (active electro-optic Q-switching) is used in the optical resonant cavity to output the dynamic laser with the pulse width of 1 μs-1.5 μs, so a loss of the resonant cavity is decreased, that is, a threshold is decreased, and an electro-optic efficiency is improved. The present disclosure realizes the output of lasers with two wavelengths via one optical path system, the short-wave laser has higher photon energy, which is conductive to the ignition of a plasma, long-wave energy is absorbed by the plasma, and the strength of a stone crushing is enhanced, and the lasers can achieve a good stone crushing effect. According to the electro-optic Q-switching double-frequency double-pulse laser lithotripsy system provided by the present disclosure, through a manner in which a sub-pulse laser beam is output by closely following a main pulse laser beam, as sub-pulse laser energy is absorbed by the generated plasma, a stone crushing strength of a shock wave is greatly enhanced; and therefore, the present disclosure may crush a cystine stone that is white and hard and cannot be crushed by a previous lithotripter. The present disclosure is an entirely independent innovation in technology, and is superior to the laser lithotripsy system at an advanced world level in function, so the present disclosure is a high-level medical system that can crush a stone having a large size, can cut the soft tissue around the stone, and has many advantages of good stone crushing effect, strong stone crushing capacity, efficient energy conversion, easiness to change the pulse width, simple structure and convenience in use, etc.

When the controller 14 controls the drive circuit 4 so that the voltage applied to the electro-optic Q-switching assembly gradually increases or decreases, a loss of the electro-optic Q-switching assembly gradually decreases and the loss of the electro-optic Q-switching assembly keeps a dynamic balance with a gain of the gain medium, the optical resonant cavity (may be referred to as a resonant cavity) always keeps basically stable laser oscillation inside, and the output mirror 7 can output the laser beam with the pulse width of 1 μs-1.5 μs. When the controller 14 controls the drive circuit 4 so that the voltage of the electro-optic Q-switching assembly is λ/4, the laser beam with the pulse width of 200 μs-300 μs is output, the λ denoting a wavelength of the laser beam output by the output mirror 7, that is, a wavelength of the laser beam output by the optical resonant cavity.

FIG. 2 is a voltage increasing type Q-switching optical path. The electro-optic Q-switching assembly includes a Pockel cell 3, a polarizer 5 and a quarter wave plate 2; the quarter wave plate 2, the Pockel cell 3 and the polarizer 5 are sequentially disposed between the total reflection mirror 1 and the gain medium; and the corresponding drive circuit 4 is referred to as a voltage increasing type Q-switching drive circuit. If the electro-optic Q-switching assembly does not include the quarter wave plate 2, a voltage dropping type Q-switching optical path is achieved, and the corresponding drive circuit is referred to as a voltage dropping type Q-switching drive circuit. The drive circuit 4 is connected to two ends of the Pockel cell 3.

In this embodiment, the gain medium is a solid laser bar 6, and specifically uses a Nd:YAG crystal. The pump source 13 uses a xenon lamp, that is, a 1064 nm laser is output, and after the 1064 nm laser is doubled by the frequency doubling crystal 12 in frequency, a 532 nm laser is obtained. The frequency doubling crystal 12 uses a KDP crystal, and the first focusing mirror 8 is configured to enhance a efficiency of frequency doubling. In this embodiment, the laser energy with an output wavelength of 1064 nm accounts for 80%, and the laser energy with the wavelength of 532 nm accounts for 20% in total energy.

Figure 3:
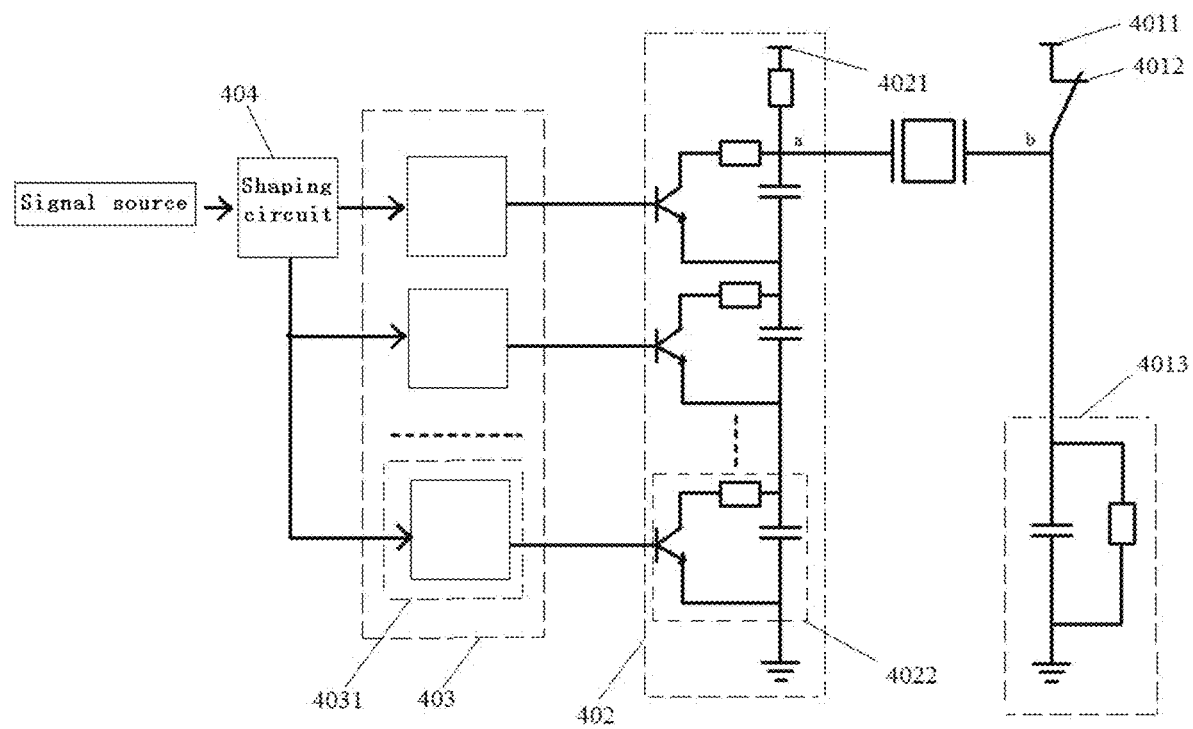
FIG. 3 is a schematic diagram of a voltage increasing type Q-switching drive circuit.

FIG. 3 is a schematic circuit of a voltage increasing type Q-switching drive circuit. The drive circuit 4 includes a shaping circuit 404, a delay drive circuit 403, a voltage dropping circuit 402 and a constant voltage circuit. The two ends of the Pockel cell 3 are loaded between output ends a and b of the voltage dropping circuit 402 and the constant voltage circuit. The constant voltage circuit is composed of a first direct-current high-voltage power supply 4011, a high-voltage switch 4012 connected to an output end of the first direct-current high-voltage power supply 4011, a filter circuit 4013 connected to the high-voltage switch 4012, and a first ground terminal connected to the filter circuit 4013. The filter circuit 4013 is formed by a capacitor and a resistor in parallel connection. The voltage dropping circuit 402 includes a second direct-current high-voltage power supply 4021, N voltage dropping sub-circuits 4022 connected to an output end of the second direct-current high-voltage power supply 4021, and a second ground terminal, wherein the N voltage dropping sub-circuits 4022 are connected serially in multiple stages. The voltage dropping sub-circuit 4022 is composed of a voltage division capacitor, a discharge current limiting resistor and a voltage division MOS switch that are connected sequentially, that is, the second direct-current high-voltage power supply 4021 and the voltage division capacitor are serially connected to the second ground terminal; and at least three voltage dropping sub-circuits 4022 are provided.

In FIG. 3, the "signal source" is a control signal output by the controller 14. The signal source is the control signal output by the controller 14. Since the signal provided by the controller 14 is a weak signal, and such parameters of the control signal as an amplitude and time cannot directly drive the subsequent delay drive circuit 403, the signal is processed necessarily. The control signal becomes an available signal to the delay drive circuit 403 after passing through the shaping circuit 404. A first delay drive signal output by a first delay drive sub-circuit 4031 in the delay drive circuit 403 forms a first stage of RC discharge loop after being loaded on a first voltage division MOS switch; and correspondingly, a voltage on two ends of a first voltage division capacitor decreases. A second delay drive signal output by a second delay drive sub-circuit 4031 in the delay drive circuit 403 forms a second stage of RC discharge loop after being loaded on a second voltage division MOS switch; and correspondingly, a voltage on two ends of a second voltage division capacitor decreases. Hereunder, a third delay drive signal output by a third delay drive sub-circuit 4031 in the drive circuit 4 and signals respectively delayed by the subsequent delay drive sub-circuits 4031 are sequentially acted on corresponding voltage division MOS switches, and the process is as above. After the delay drive circuit 403 turns on the voltage dropping sub-circuit 4022 sequentially, a potential at the a point of the output end of the voltage dropping circuit 402 gradually decreases. As the b point on the output end of the constant voltage circuit keeps unchanged at a high potential, the voltage on the two ends of the Pockel cell 3 gradually increases. Such a manner is the voltage increasing type electro-optic Q-switching (that is, voltage increasing type Q-switching) manner. Since the Pockel cell 3 is communicated with the a and the b, the a point serves as both the output end of the voltage dropping circuit 402 and a voltage transformation end of the Pockel cell 3, and the b point serves as both the output end of the constant voltage circuit and a constant voltage end of the Pockel cell 3. Herein, voltage dropping type electro-optic Q-switching may also be available. If the voltage dropping type electro-optic Q-switching (that is, voltage dropping type Q-switching) is used, the b point on the constant voltage end of the Pockel cell 3 in FIG. 3 is directly grounded, that is, the constant voltage circuit only includes the first ground terminal. In this way, as the voltage dropping circuit 402 is turned on sequentially, the potential at the a point on the voltage transformation end of the Pockel cell 3 decreases gradually, and the potential on the constant voltage end is zero all the time. Therefore, a voltage on the two ends of the Pockel cell 3 still trends to decline, to implement the voltage dropping type electro-optic Q-switching. For the voltage dropping sub-circuit 4022 corresponding to the delay drive signal of each delay drive sub-circuit 4031, the delay drive sub-circuit 4031 is the same as the voltage dropping sub-circuit 4022 in quantity. Each delay drive sub-circuit 4031 and the delay drive signal sent therefrom, and each voltage dropping sub-circuit 4022 and an internal element thereof are all named by "first", "second", "third" and the like, which is only schematic to distinguish the sequence and the element.

Figure 4:
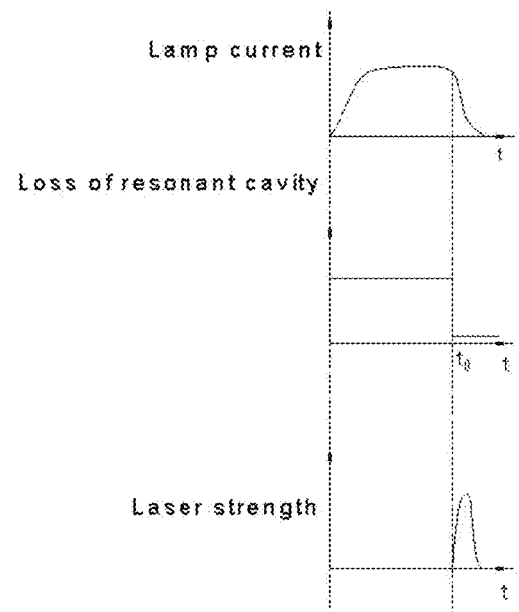
FIG. 4 is a graph of a waveform of a light, a loss of an optical resonant cavity and a waveform of a laser intensity for a conventional fast switching electro-optic Q-switched xenon lamp.

According to a common sense of a laser technology, a conventional electro-optic Q-switching/electro-optic Q-switching assembly is a fast switching, and an output laser pulse width is generally up to a nanosecond level. As shown in FIG. 4 that is an oscillogram showing a waveform of light(lamp current), a loss of an optical resonant cavity and a waveform of a laser strength for a traditional quick electro-optic Q-switching voltage increasing xenon lamp, the waveform of the light is in a flat-topped distribution along with the time, a discharge current of the xenon lamp at a $t_0$ moment starts to decrease, a loss of the optical resonant cavity decreases quickly, and a gain in the loss of the optical resonant cavity is greater than the loss of the optical resonant cavity; and thus, an optical pulse with large energy and a narrow pulse width is generated.

In order to implement continuous output of a 1 μs laser, the increase or decrease of the voltage on the Pockel cell 3 cannot be too fast or too slow, and the loss of the electro-optic Q-switching assembly keeps a dynamic balance with the gain of the gain medium, so that laser oscillation in the cavity is basically stable all the time, until the laser output reaches about 1 μs. To implement the continuous output of the 1 μs laser, it is necessary that a speed of the increase (or decrease) of the voltage on the Pockel cell 3 is appropriate, and when the storage energy of the solid laser bar 6 is reduced or improved, the speed of the increase (or decrease) of the voltage is also subjected to change correspondingly. In the present disclosure, one end of the Pockel cell 3 is loaded on the output end of the voltage dropping circuit 402 that is connected serially in multiple stages, and the other end of the Pockel cell 3 is loaded on the output end of the constant voltage circuit. The voltage dropping circuit 402 is turned on in sequence by means of an external control signal, so that a voltage on two ends of the voltage dropping circuit 402 gradually decreases, and at last a voltage on two ends of the Pockel cell 3 increases (or decreases) stage by stage. The discharge current-limiting resistor in the voltage dropping sub-circuit 4022 determines a voltage dropping speed at each stage in the serially-connected voltage dropping sub-circuit 4022, and the delay drive sub-circuit 4031 controls a voltage dropping delay, that is, the voltage dropping speed at each stage of the voltage dropping circuit 402 is controllable, and the voltage dropping delay at different stages is adjustable. With the control of the controller 14 and the drive circuit 4, the laser oscillation is basically stable; and at last, the smooth output of 1 μs-1.5 μs is implemented, and a peak value of a top oscillation is smaller than 10% of a total amplitude.

Figure 5:
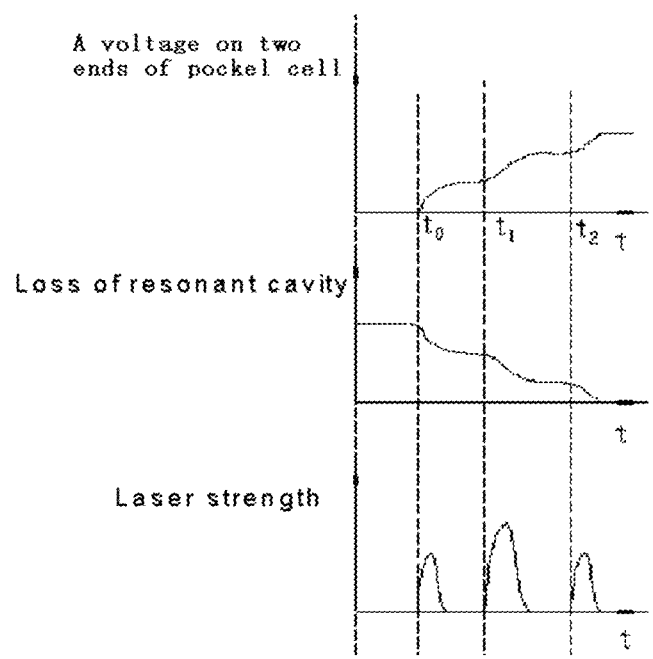
FIG. 5 is a schematic diagram showing a mechanism that a slow switching voltage increasing type Q-switching drive circuit controls output of a laser.

The implementation method and principle are as follows. By applying a voltage increasing type Q-switching drive circuit shown in FIG. 3, a method for decreasing a switching speed is used to output the laser with the pulse width of 1 μs. The generation mechanism of the laser is as shown in FIG. 5, which is a schematic diagram showing a mechanism that a slow voltage increasing type Q-switching drive circuit controls output of a laser. As can be seen from FIG. 5, with $0$-$t_0$ time, the xenon lamp pumps the solid laser bar 6, a number of upper level reversal particles in the solid laser bar 6 increases constantly, a voltage on the two ends of the Pockel cell 3 is zero, the loss of the optical resonant cavity is very high, the solid laser bar 6 stores the energy, and no laser is emitted. Within $t_0$-$t_1$ time, a voltage on the two ends of the Pockel cell 3 gradually increases, the loss of the optical resonant cavity is smaller than the gain, the optical resonant cavity starts to output the laser, the upper level reversal particles are consumed partially, and when the gain is smaller than the loss, the oscillation stops, and a first optical pulse is output. Within $t_1$-$t_2$ time, a voltage on the two ends of the Pockel cell 3 increases again slowly, the loss of the optical resonant cavity is further reduced, the gain is greater than the loss, a part of reversal particles are consumed continuously, and the optical resonant cavity is oscillated again. In this way, a second pulse is generated; and by parity of reasoning, multiple optical pulses are generated at last. The number of output optical pulses is the same as the number of times that a voltage on the two ends of the Pockel cell 3 increases. A width of each optical pulse and an amplitude of the increase of the voltage are dependent on the speed of the increase of the voltage. A corresponding light emitting mechanism of the voltage dropping type Q-switching drive circuit is the same as that of the voltage increasing type.

Figure 6:
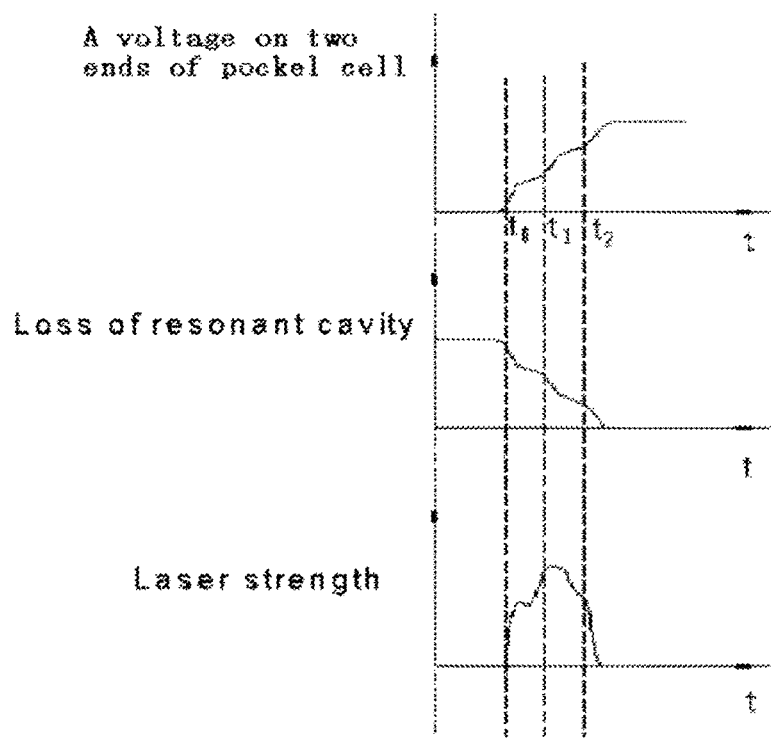
FIG. 6 is a schematic diagram showing that a slow switching voltage increasing type Q-switching drive circuit controls output of a single pulse laser.

FIG. 6 is a schematic diagram showing that a slow switch voltage increasing type Q-switching drive circuit controls output of a single pulse laser. In order to obtain a smooth optical pulse of about 1 μs, the trigger delay of a voltage division MOS switch is appropriate adjusted relative to FIG. 5, that is, by changing delay time of a control signal for turning on front and rear voltage division MOS switches, an interval between discharge moments of front and rear cascade circuits, such as the interval between $t_0$ and $t_1$ and between $t_1$ and $t_2$, changes, thus accelerating the speed of increase of a voltage on the two ends of the Pockel cell 3; that is, by adjusting the speed of decrease of the loss of the optical resonant cavity, several different optical pulses are overlapped to each other at last to integrate into one optical pulse with the pulse width of about 1 μs to output.

In the voltage dropping type electro-optic Q-switching, a voltage on two ends of the Pockel cell 3 is reverse to the output waveform of the voltage increasing type Q-switching drive circuit (a voltage on the two ends of the Pockel cell 3), whereas waveforms for the loss of the optical resonant cavity and the laser strength along with the time are the same.

The above FIGS. 4-6 schematically show a relationship along with the time, so a specific unit is not given on a vertical coordinate.

The lithotripsy system provided by the present disclosure is applied to the following several cases.

1. Case where a Q-switching dynamic laser is output necessarily for stone crushing Voltage increasing type Q-switching drive circuit: when the Q-switching dynamic laser is output necessarily for stone crushing, the controller 14 controls ignition of the pulse xenon lamp and applies a high voltage of a λ/4 wave (about 3400 V) to the a end and the b end of the Pockel cell 3, and the difference between a voltage on the two ends of the Pockel cell 3 is zero. Due to the presence of the quarter wave plate 2, the resonant cavity is closed, and the solid laser bar 6 stores the energy. After a delay of about 300 μs, the controller 14 sends a control signal to turn on the delay drive sub-circuit 4031 sequentially stage by stage, the voltage on a voltage division capacitor of each voltage dropping sub-circuit 4022 decreases sequentially, and the voltage on the a end of the Pockel cell 3 decreases gradually; and after the last delay drive sub-circuit 4031 is turned on, the a end of the Pockel cell 3 is grounded, and the b end of the Pockel cell 3 still has the voltage of the λ/4 wave. During this process, the difference of the voltage on the two ends of the Pockel cell 3 increases slowly; and by adjusting interval time of different delay signals, the speed of decrease of a voltage on the two ends of the voltage division capacitor in the voltage dropping sub-circuit 4022 may be adjusted.

Voltage dropping type Q-switching drive circuit: the potential on the b end of the Pockel cell 3 is 0 V all the time, and the voltage on the a end decreases gradually. In this way, a voltage loaded on the two ends of the Pockel cell 3 decreases gradually, to output a laser of a voltage dropping Q-switching optical path.

2. Case where a static laser is output necessarily for stone crushing

Figure 7:
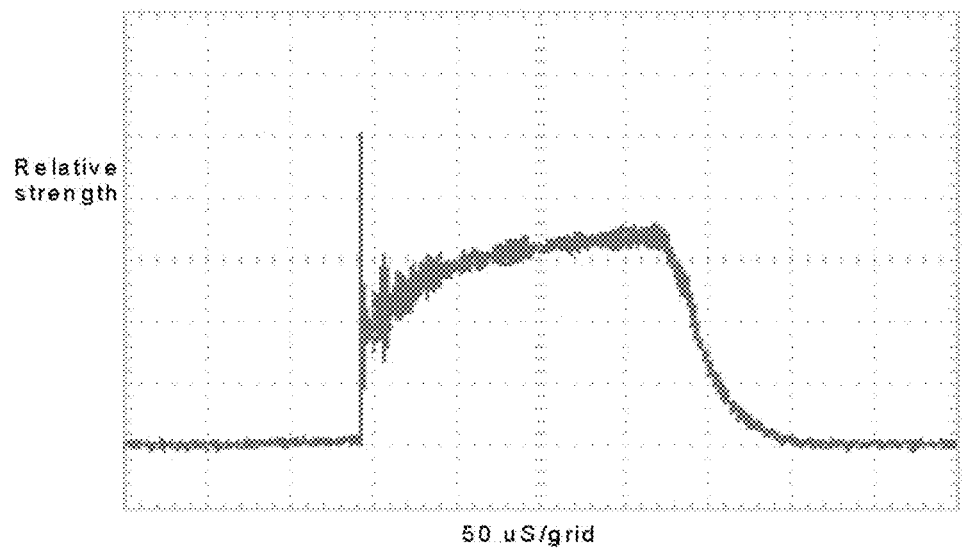
FIG. 7 is a waveform of a static laser for stripping a soft tissue.

In such a case, the electro-optic Q-switching assembly does not control the loss of the optical resonant cavity, that is, non-Q-switching. For the voltage increasing type Q-switching drive circuit, the controller 14 does not send the control signal, the high-voltage switch 4012 is turned off, the b end of the Pockel cell 3 is grounded and the a end of the Pockel cell 3 still has the voltage of the λ/4 wave, the optical resonant cavity is located in a free oscillation state, and the static laser as shown in FIG. 7 is output to strip the soft tissue. For the voltage dropping type Q-switching drive circuit, the power supply of a high-voltage source is disconnected by means of a control system, the output of each of external two high-voltage sources is 0, a voltage on the two ends of the Pockel cell 3 is 0 V, and the static laser output by the voltage increasing type Q-switching drive circuit and shown in FIG. 7 may still be output.

Figure 8:
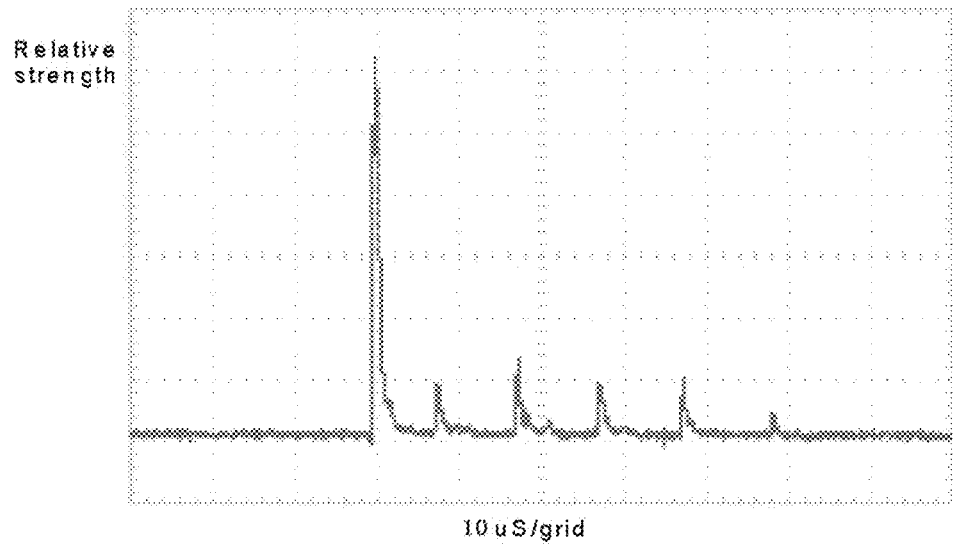
FIG. 8 is a waveform of a sub-pulse laser closely-followed a dynamic laser.

3. Case where pulse energy of a closely followed sub-pulse laser of the dynamic laser changes necessarily When it is necessary to change the pulse energy of the sub-pulse laser closely following the dynamic laser, only a delay for turning on the electro-optic Q-switching assembly needs to be changed. If the electro-optic Q-switching assembly is turned on in advance, as the xenon lamp pumps continuously, energy of a subsequent sub-pulse laser increases. If the electro-optic Q-switching assembly is turned on with a delay, as the pump of the xenon lamp is nearly ended, the energy of the subsequent sub-pulse laser decreases, as shown in FIG. 8 that is an oscillogram of a sub-pulse laser closely following a Q-switching dynamic laser in the present disclosure.

What is claimed is:

1. An electro-optic Q-switching double-frequency double-pulse laser lithotripsy system, comprising a total reflection mirror (1), an electro-optic Q-switching assembly, a drive circuit (4), a controller (14), a pump source (13), a gain medium (6), an output mirror (7), a first focusing mirror (8), a frequency doubling crystal (12), a second focusing mirror (9), a coupling lens (10) and an output optical fiber (11), wherein the electro-optic Q-switching assembly and the gain medium (6) are located between the total reflection mirror (1) and the output mirror (7); the drive circuit (4) is connected to the electro-optic Q-switching assembly; and the controller (14) is connected to the electro-optic Q-switching assembly and the pump source (13), the controller (14) controls the pump source (13) to work, and the controller (14) controls a voltage of the electro-optic Q-switching assembly by controlling the drive circuit (4); and the controller (14) controls the pump source (13) to generate pump light to irradiate the gain medium (6); the controller (14) controls the drive circuit (4); when a voltage difference exists on the electro-optic Q-switching assembly, an optical resonant cavity is formed between the total reflection mirror (1) and the output mirror (7); when the pump light passes through the optical resonant cavity and a gain of the pump light reaches a threshold, a laser beam is output by the output mirror (7); the laser beam is sequentially converged by the first focusing mirror (8), partially doubled in frequency by the frequency doubling crystal (12), and then emitted in parallel via the second focusing mirror (9), converged and coupled by the coupling lens (10), and output through the output optical fiber (11); and the laser beam is a dynamic laser beam with a pulse width of 1 µs-1.5 µs or a static laser beam with a pulse width of 200 µs-300 µs.

2. The electro-optic Q-switching double-frequency double-pulse laser lithotripsy system as claimed in claim 1, wherein when the voltage of the electro-optic Q-switching assembly gradually increases or decreases, a loss of the electro-optic Q-switching assembly gradually decreases, and the loss of the electro-optic Q-switching assembly keeps a dynamic balance with a gain of the gain medium (6) all the time, the output mirror (7) outputs the laser beam with a pulse width of 1 µs-1.5 µs; when the voltage of the electro-optic Q-switching assembly is λ/4, the output mirror (7) outputs the laser beam with a pulse width of 200 µs-300 µs, wherein the λ denotes a wavelength of the laser beam output by the output mirror (7).

3. The electro-optic Q-switching double-frequency double-pulse laser lithotripsy system as claimed in claim 1, wherein the electro-optic Q-switching assembly comprises a Pockel cell (3) and a polarizer (5), and the drive circuit (4) is connected to two ends of the Pockel cell (3).

4. The electro-optic Q-switching double-frequency double-pulse laser lithotripsy system as claimed in claim 3, wherein the electro-optic Q-switching assembly further comprises a quarter wave plate (2), the quarter wave plate (2) is located between the total reflection mirror (1) and the Pockel cell (3), and when a voltage of the two ends of the Pockel cell (3) gradually decreases, a loss of the Pockel cell (3) gradually decreases and the loss of the Pockel cell (3) keeps a dynamic balance with the gain of the gain medium (6) all the time, the laser beam with a pulse width of 1 µs-1.5 µs is output.

5. The electro-optic Q-switching double-frequency double-pulse laser lithotripsy system as claimed in claim 3, wherein the drive circuit (4) comprises a shaping circuit (404) connected to the controller (14), a delay drive circuit (403) connected to the shaping circuit (404), a voltage dropping circuit (402) connected to the delay drive circuit (403) and one end of the Pockel cell (3), and a constant voltage circuit connected to other end of the Pockel cell (3), the voltage dropping circuit (402) comprises a second direct-current high-voltage power supply (4021), N voltage-dropping sub-circuits (4022) and a second ground terminal that are serially connected in sequence, the second direct-current high-voltage power supply (4021) is serially connected to the N voltage-dropping sub-circuits (4022), the delay drive circuit (403) comprises N delay drive sub-circuits (4031), and the delay drive sub-circuits (4031) are connected to the voltage-dropping sub-circuits (4022) in one-to-one correspondence, N≥3.

6. The electro-optic Q-switching double-frequency double-pulse laser lithotripsy system as claimed in claim 5, wherein the constant voltage circuit comprises a first ground terminal.

7. The electro-optic Q-switching double-frequency double-pulse laser lithotripsy system as claimed in claim 6, wherein the constant voltage circuit further comprises a first direct-current high-voltage power supply (4011), a high-voltage switch (4012) connected to an output end of the first direct-current high-voltage power supply (4011), and a filter circuit (4013) connected to the high-voltage switch (4012), and the first ground terminal is connected to the filter circuit (4013).

8. The electro-optic Q-switching double-frequency double-pulse laser lithotripsy system as claimed in claim 7, wherein the filter circuit (4013) is formed by a capacitor and a resistor in parallel connection.

9. The electro-optic Q-switching double-frequency double-pulse laser lithotripsy system as claimed in claim 5, wherein the voltage-dropping sub-circuit (4022) comprises a voltage-division Metal Oxide Semiconductor (MOS) switch, a voltage-division capacitor and a discharge current limiting resistor that are connected sequentially, and the voltage-division MOS switch is connected to a corresponding delay drive sub-circuit (4031).

10. The electro-optic Q-switching double-frequency double-pulse laser lithotripsy system as claimed in claim 1, wherein the pump source (13) is a xenon lamp, and the gain medium (6) is a Nd:YAG crystal.

* * * * *